United States Patent
Kuhl et al.

(10) Patent No.: US 10,500,369 B2
(45) Date of Patent: Dec. 10, 2019

(54) SYSTEM AND METHOD OF STRESS REDUCTION

(71) Applicant: Waterfalls Day Spa, Inc., Middlebury, VT (US)

(72) Inventors: Sarah Kuhl, Middlebury, VT (US); Laurie Webb, Middlebury, VT (US); Sara Daly, Middlebury, VT (US)

( * ) Notice: Subject to any disclaimer, the term of this patent is extended or adjusted under 35 U.S.C. 154(b) by 111 days.

(21) Appl. No.: 15/557,091

(22) PCT Filed: Mar. 14, 2016

(86) PCT No.: PCT/US2016/022323
§ 371 (c)(1),
(2) Date: Sep. 11, 2017

(87) PCT Pub. No.: WO2016/149192
PCT Pub. Date: Sep. 22, 2016

(65) Prior Publication Data
US 2018/0050170 A1 Feb. 22, 2018

Related U.S. Application Data

(60) Provisional application No. 62/133,329, filed on Mar. 14, 2015.

(51) Int. Cl.
*A61M 21/00* (2006.01)
*A61M 21/02* (2006.01)
*G06F 19/00* (2018.01)

(52) U.S. Cl.
CPC ......... *A61M 21/02* (2013.01); *G06F 19/3481* (2013.01); *A61M 21/00* (2013.01); *A61M 2021/005* (2013.01); *A61M 2021/0016* (2013.01); *A61M 2021/0022* (2013.01); *A61M 2021/0027* (2013.01); *A61M 2021/0044* (2013.01); *A61M 2205/3553* (2013.01); *A61M 2205/3584* (2013.01);
(Continued)

(58) Field of Classification Search
CPC .... A61M 21/00; A61M 21/02; G06F 19/3481
USPC ...................................... 600/26–28
See application file for complete search history.

(56) References Cited

U.S. PATENT DOCUMENTS 5,304,112 A 4/1994 Mrklas et al.
6,484,062 B1 11/2002 Kim
(Continued)

FOREIGN PATENT DOCUMENTS

WO 2000062850 A1 10/2000

OTHER PUBLICATIONS

Cohen, "Perceived Stress Scale", 1994.

*Primary Examiner* — John P Lacyk
(74) *Attorney, Agent, or Firm* — Justin W. McCabe, Esq.; Dunkiel Saunders Elliott Raubvogel & Hand, PLLC

(57) ABSTRACT

The present disclosure provides a synergistic system and protocol for stress management and reduction in a person in need thereof. In particular, an improved system and method for relaxing, reducing stress in, and improving the well-being of an individual is disclosed such that after treatment or use of the system the individual can recall or come back to a decreased stress state obtained during treatment, thereby reducing their present stress level. It is an objective of the present invention to provide a non-pharmaceutical method and system of treatment that merges several stress reduction methods into an effective treatment protocol that can be used in a variety of environments and on any age of individual as a means to reduce anxiety and stress.

18 Claims, 3 Drawing Sheets

(52) U.S. Cl.
CPC ............... *A61M 2205/3592* (2013.01); *A61M 2205/502* (2013.01); *A61M 2205/52* (2013.01)

(56) References Cited

U.S. PATENT DOCUMENTS

| | | |
|---|---|---|
| 2005/0283100 A1 | 12/2005 | Whittier |
| 2010/0331607 A1 | 12/2010 | Pelgrim et al. |
| 2011/0070571 A1 | 3/2011 | Verkuilen |
| 2013/0211277 A1 | 8/2013 | Berg et al. |

SYSTEM AND METHOD OF STRESS REDUCTION

RELATED APPLICATION DATA

This application claims the benefit of priority of U.S. Provisional Application No. 62/133,329, filed Mar. 14, 2015, and titled "System and Method of Stress Reduction", which is incorporated by reference herein in its entirety.

FIELD OF THE INVENTION

The present invention generally relates to the treatment of stress. In particular, the present invention is directed to a system and method of stress reduction provided by synergistic multi-sensual stimuli combined with a stress reduced recall stimuli.

BACKGROUND

Chronic stress can have a causal health impact or, in many people, can exacerbate existing health conditions. Stress affects the physiology and the psychology of an individual and can have a profound negative effect on their overall wellness. As people feel increasingly more pressured, exacting, competitive, and hurried in their ever more hectic daily lives, mental and physical stress is growing and the need for ways for people to cope with stress, release anxiety, and find relaxation are concomitantly increasing.

Unfortunately, too many people are unable to extricate themselves from their hurried routines and find their only break in different forms of stressful endeavor. For example, people who look to release tension through physical exercise will frequently only add to their overall mental stress as the activity becomes time consuming or controlling. Conversely, even passive activities which are considered by many to be both physically and emotionally peaceful and relaxing may often create additional stress. This stress may result from the mental involvement in games where players are pitted against other players; from fright or distress induced through distressing media; mental involvement in sports competition; and personal or emotional involvement in the story line of movies, shows and the like.

Numerous books and papers have been written on ways to relieve stress and anxiety. In addition, exercise systems, biofeedback systems and the like have been developed to assist in obtaining both physical and mental relaxation. Normally, such systems are employed in conjunction with physical devices which are designed to stimulate the senses, and are generally intended to provide an environment for the individual that shuts out outside interferences.

Alternatively, some people attempt to remove themselves from daily duties and other activities, by, for example, attending resorts or secluded hideaways where there is time to relax and peaceful surroundings. Others have sought various forms of controlled physical exercise in an effort to find an escape from stress. For example, health spas cater not only to physical exercise but provide hot tubs and saunas and the like to relieve tensions and ease muscles. However, these are time intensive and expensive activities that are not readily accessible to all those who need assistance with stress reduction.

Lastly, use of psychotropic drugs to treat symptoms of stress can have negative side effects and are not necessarily an effective means to manage day to day stress.

It is well known that there is a relationship between stress, especially chronic stress, and a person's health and well-being. And while, as discussed above, there are treatments and coping techniques that have shown some success in reducing stress levels, these treatments and techniques lack potency. Thus there is a need for treatments to reduce stress and anxiety in individuals as part of their stress management program that are powerful, easy to access, effective, quick, and versatile in use.

SUMMARY OF THE DISCLOSURE

In a first exemplary aspect, there is disclosed a method for reducing stress comprising administering a synergistically effective therapeutic amount of a visual stress reduction stimulus, an olfactory stress reduction stimulus, an auditory stress reduction stimulus, and a tactile stress reduction stimulus to a person in need thereof.

In another exemplary aspect, there is disclosed a treatment method for treating stress in a person in need thereof comprising: receiving, as an input, information related to the stress experienced by the person; selecting a stress modifier program based upon the information; and exposing the person to synergistically effective amount of a multi-sensory stimuli, the multi-sensory stimuli being associated with the stress modifier program, wherein the multi-sensory stimuli include at least one visual stimulus, at least one olfactory stimulus, at least one auditory stimulus, and at least one tactile stimulus.

In yet another exemplary aspect, there is disclosed a system for treatment of stress in a person, the system comprising: a multi-sensory stimuli delivery system; and a computing device in communication with the multi-sensory stimuli delivery system including a processor and a database, the database including a media data portion, a visual data portion, an olfactory data portion, and a tactile data portion, the processor including a set of instructions to: receive, as an input, information related to the stress experienced by the person; and determine a stress modifier program based upon the information, direct the multi-sensory stimuli delivery system to expose the person to multi-sensory stimuli, the multi-sensory stimuli being associated with the stress modifier program, wherein the multi-sensory stimuli include at least one visual stimulus, at least one olfactory stimulus, and at least one auditory stimulus.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DESCRIPTION OF THE DISCLOSURE

Figure 1:
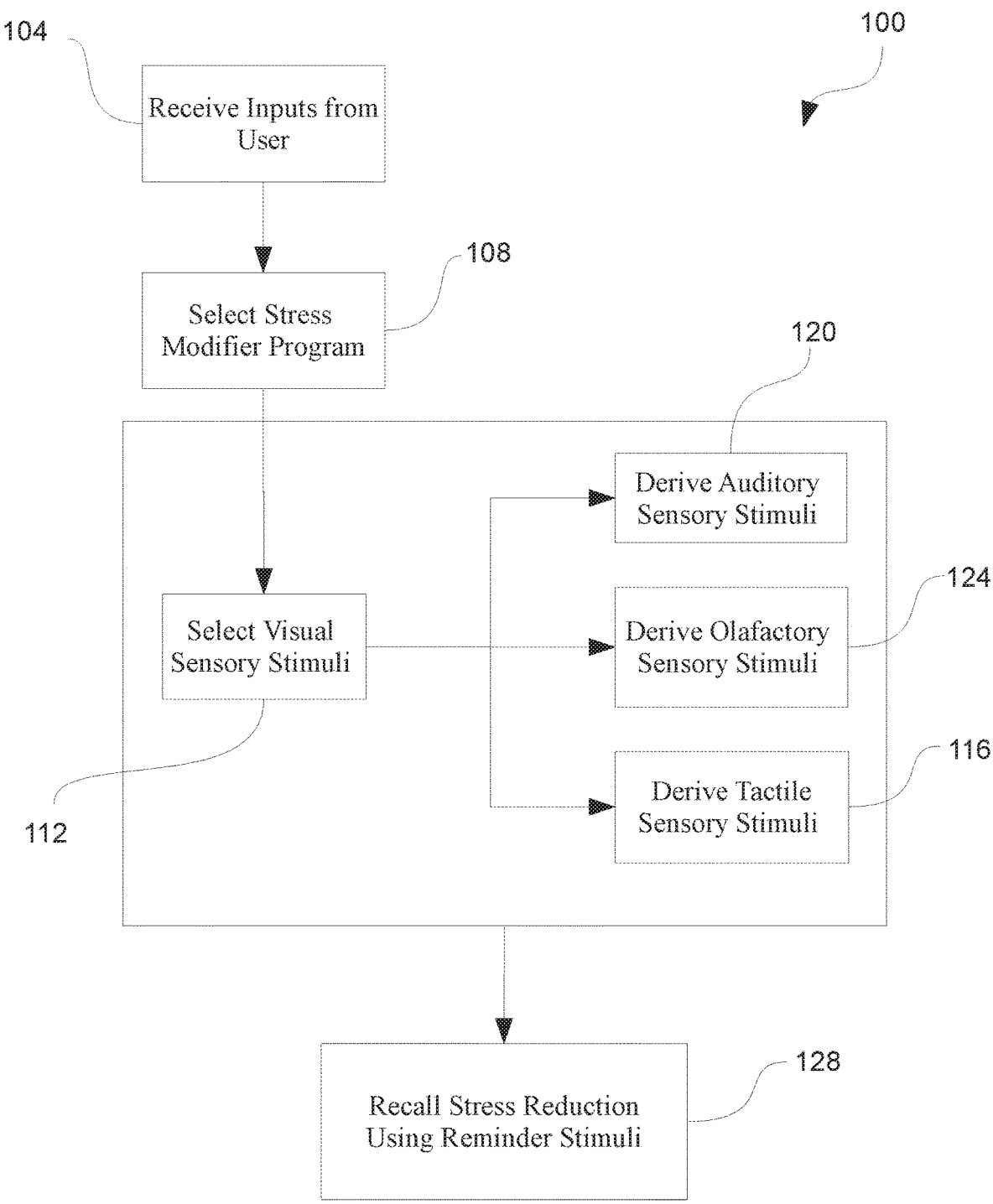
FIG. 1 shows a process diagram of an exemplary method of reducing stress according to an embodiment of the present invention.

A system and method of stress reduction according to the present disclosure provides a synergistic system and protocol for stress management and reduction. In particular, an improved system and method for relaxing, reducing stress in, and improving the well-being of an individual is disclosed such that after treatment or use of the system the individual can recall or come back to a decreased stress state obtained during treatment, thereby reducing their present stress level. It is an objective of the present invention to provide a non-pharmaceutical method and system of treatment that synergistically merges therapeutic amounts of several stress reduction methods into an effective treatment protocol that can be used in a variety of environments and on any age of individual as a means to reduce anxiety and stress.

In certain embodiments, the present invention involves exposing the individual to an interrelated and synergistic combination of scent, color, sound, and guided meditation. Certain embodiments of the present invention can involve exposing the individual to an interrelated and synergistic combination of scent, in the form of aromatherapy, color therapy, music, massage, visual images and/or photography, and guided visualization or imagery. Embodiments disclosed herein are shown to reduce stress in users in need thereof significantly more than the individual application of treatment options discussed herein. Moreover, a system, suitable for performing the method, is also disclosed, wherein the system delivers multi-sensory stimuli to a person in need thereof, the multi-sensory stimuli being selected and guided by the person's needs.

Before turning to the figures, a brief summary of the principal components of the treatment method is discussed below.

Aromatherapy

Aromatherapy is the practice of using natural oils or other volatile compounds to enhance psychological and physical well-being. Aromatherapy traditionally works primarily through the nose, but can also act through the lungs and the skin. When inhaled, volatile aroma compounds (typically from plants) are capable of exerting direct-to-brain actions, primarily through the limbic and olfactory systems. As opposed to the oral ingestion or topical application of a drug or herbal substance, aromatherapy usually offers a far higher margin of safety because the active compounds are small molecules.

Guided Meditation

Guided Meditation is a process by which one or more participants meditate in response to guidance provided by a trained practitioner or teacher, either in person or via a written text, sound recording, video, or audiovisual media comprising music or verbal instruction, or a combination of both.

Color Therapy

Generally, color therapy is the therapeutic use of colors. Color therapy typically encompasses a number of methods including, but not limited to, the direction of light of specific colors at the chakras (centers of spiritual power in the human body) associated with the color the stimulation of acupoints (locations that are the focus of acupuncture), and the use of light of specific wavelengths to facilitate healing. Color therapy is sometimes employed as a complementary treatment for seasonal affective disorder, depression, and stress.

Massage

Massage refers to rubbing and pressing on the skin and muscles using variety of techniques, for example, Swedish massage. The benefits of massage are well known, but have been used to treat stress and the symptoms of stress like headaches and muscle tension or pain.

Calming Music

Music has used to calm people for hundreds of years at is has a link to human emotions. Music has been shown to have a beneficial effect on physiological functions, e.g., slowing the pulse and heart rate, lowering blood pressure, and decreasing the levels of stress hormones.

Calming Photos/Nature Photos

Research has shown that taking a walk in a natural setting can reduce anxiety, for example, a 20% increase in focus was found in subjects that paused for break in an arboretum when compared to those who paused on a busy street. In another study, subjects were asked to take a break and either look at pictures of a nature scene or a city street. The break to look at a nature scene resulted in an increase in focus. Although not a substitute for being in nature, seeing photos of nature has been shown to have a positive effect on people's well-being and reduces their stress levels.

Turning now to the figures, and specifically, with reference to FIG. 1, there is shown an exemplary treatment method 100 according to an embodiment of the present invention. At a high level, method 100 provides a synergistic application of multi-sensory stimuli stress reduction treatments so as to reduce the stress level in the individual using the method. Furthermore, the method includes the ability of the person who has received the treatment to recall, after the primary treatment is completed, the relaxed stress state achieved.

At step 104, a user, operator, or person provides inputs regarding their stress and proclivities. For example, a user can provide input regarding the type of stress being felt (e.g. chronic, acute, light, etc.) and how the user is feeling. In an exemplary embodiment, the user is prompted to answer a series of questions that facilitate an understanding about the type of stress the user is feeling, the types of treatments previously received, and the user's current state-of-mind. In another exemplary embodiment, the user is asked to look at a plurality of images and to select one that is most appealing.

At step 108, a stress modifier program is selected from a database of stress modifier programs. Stress modifier programs are developed and selected based upon, for example, the level of stress felt by the user, the type of stress (e.g., chronic, acute, etc.), and the inclinations of the person (how the person is feeling at the moment). Thus, when a user engages with method 100, the method provides stress modifier programs that are designed and configured to meet the person's individual needs.

In an exemplary embodiment, each stress modifier program is guided by the selection of one of the components of the program. Thus, for example, and in an exemplary embodiment, the selection of the stress modifier program is based in part upon the person's selection of a visual element from a database of visual elements at step 112. This selection, in turn, (and optionally based upon the previously received user inputs) results in a coordination between the other treatments to provide a synergistic stress reducing combination of treatments.

The database of visual elements provided at step 112 can include, but is not limited to, an image of a scenic setting, an object, a person, etc. In another embodiment, the selection is made from a color on a color palette. The color can be chosen from a variety of colors that are displayed to the user or the user can chose a color, such as a color that relates to how they are currently feeling or are in need of feeling. For example, a person may decide to choose a red color if they are desirous of or feeling passionate. In alternative embodiments, the inputs received at step 104 may influence the types of colors selectable by the user.

As mentioned above, the selection of an image or color (or of other stimuli, e.g., a scent, a sound, etc.) at step 112 can then set in motion and dictate the additional stress reduction stimuli discussed herein. In an exemplary embodiment, the color or image chosen at step 112 has associated with the color or image, at least one tactile stimulus 116, at least one auditory stimulus 120, and at least one olfactory stimulus 124.

Tactile stimuli can include, but are not limited to, massage, vibration and the like or combinations of the same.

Auditory stimuli can include, but are not limited to, music, guided meditation, natural soundscapes and the like or combinations of the same.

Olfactory stimuli can include, but are not limited to, essential oils in the form of mists and lotions, natural fragrances, perfumes, toilette waters and the like or combinations of the same.

Exemplary combinations, include, for example, after the selection of the color red, the provision of a meditation designed and configured to relate to the passion and cardiovascular system of the user, the provision of a ginger and cassis scented oil and massage, music orchestrated to be passionate, and imagery and/or color exposure within the red palate. Additional multi-sensory combinations are disclosed in previously incorporated U.S. Provisional Application No. 62/133,329, filed Mar. 14, 2015, and titled "System and Method of Stress Reduction", which, for avoidance of doubt, is incorporated by reference for its discussion and images of the same.

The benefits determined via the method outlined above is that the related stimuli (the stimuli that are related to the initial selection) synergistically enhance the stress reduction experienced by the user. The selection and implementation of the stimuli for each stress reduction program are determined by relating the attributes/associations between the different stimuli. For example, and as mentioned above, the color red is associated with passion, love, energy, and adventure. Thus, to coordinate with the color red, a scent is chosen which has similar attributes. In this example, ginger has been associated with passion, success, and power. Similarly, the guided meditation and visualization aspects of the stress reduction program are designed to reinforce and supplement these attributes. Experimental studies by the inventors (discussed in more detail below) have shown that the combination of the stimuli as discussed herein leads to a greater than expected impact on stress reduction than would be expected from implementing each stimulus individually.

The stress reduction of treatment method 100 is further enhanced with the inclusion of a recall stimulus that is provided to the user proximate the end of the treatment session at step 128. The recall stimulus can be an object, such as, but not limited to, a bracelet, a picture, a stone, a lotion, a mist, or the like. In a preferred embodiment, the recall stimulus is an object that the person under receipt of the treatment has access to readily. For example, a user may be given a scented bracelet as part of the treatment system, the color and scent of the bracelet being related to the visual and tactile stimuli received during the stress reduction treatment. In this way, a user can look to, feel, or smell the recall stimulus, as desired, and recall the treatment and the de-stressed state that resulted from the treatment, and accordingly the treatment method is further enhanced.

Figure 2:
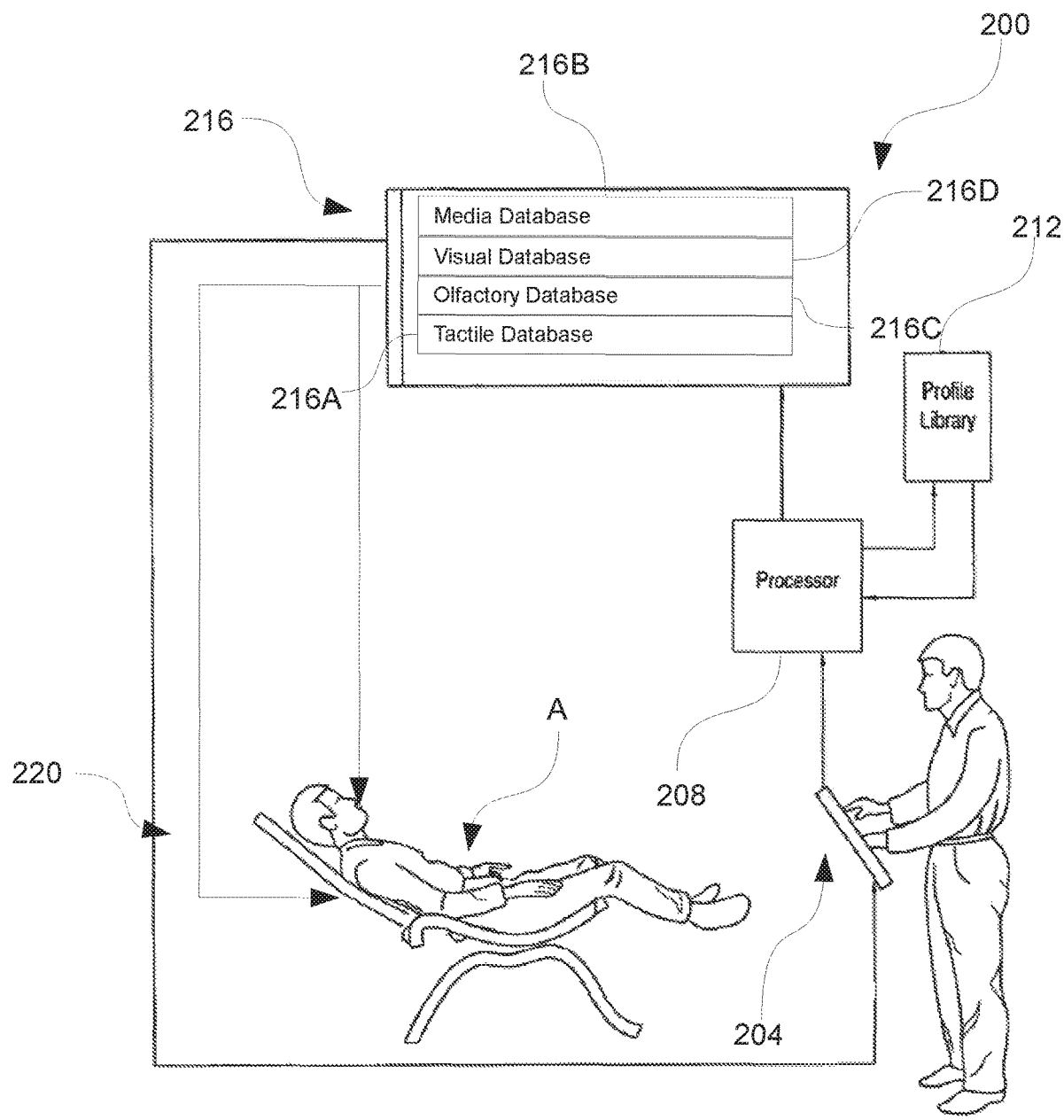
FIG. 2 shows a diagram of a system of reducing stress according to the present invention.

An exemplary treatment system 200 is shown in FIG. 2. At a high level, treatment system 200 includes a computing device 204 that includes a processor 208 and a profile library 212 and a plurality of database 216 in communication with the processor. System 200 also includes a treatment delivery module 220 for providing the synergistic treatment to a user (labeled as "A"). In an exemplary embodiment of treatment system 200, after selection of the stress modifier program using computing device 204 (and after for example, receiving inputs from the user A), the system selects from among the databases of information, e.g., tactile database 216A, media database 216B, olfactory database 216C, and visual database 216D, the appropriate stimuli to de-stress the user. In an exemplary embodiment, the stimuli are selected based upon an initial selection of one of the stimuli. For example, if the user selects a specific mediation exercise, this mediation exercise is associated with certain other stimuli that will enhance the effect of the mediation and greatly reduce the stress of the user.

Delivery module 220 is generally designed and configured to deliver the synergistic multi-sensory treatments described herein. For example, and as shown in FIG. 2, delivery module 220 can be a massage chair that provides particular massage techniques based the stress reduction program. Delivery module 220 can also include speakers for providing guided mediation and/or music, a scent dispenser for releasing essential oils to be inhaled by the user, and a display screen that can provide a visual stress reducer. In another embodiment, delivery module 220 includes a virtual reality headset with integrated speakers and scent dispensing capabilities so as to allow for complete immersion of the user in the environment. In this embodiment, massage can be provided external to the virtual reality headset.

Profile library 212 can include a database of information that stores the prior stress reduction stimuli used in treatment for the particular user. Profile library 212 can be used to determine future options or stimuli for stress reduction based on predetermined criteria or past use by the user.

Experiment 1: Perceived Stress Reduction:
Comparison of Single Modality Treatment Versus
Multiple Modality Treatment Explanation of Method A study was conducted to compare known stress reduction methods to that of an exemplary embodiment of method 100 (FIG. 1) (referred to below as method 100 for ease of reading). Participants in the study were recruited through an advertisement for volunteers. Twenty-seven individuals with age range from 18 to 73 with a mean age of 50.4 participated. Participants were asked to complete a questionnaire upon arrival in a neutral environment with no photos, neutral colors, at a plain table. Sheldon Cohen's Perceived Stress Scale was used to gather baseline chronic stress for the previous 30 days and for comparison.

Participants were then asked to give a number between 0 and 10 as to their current stress level, 0 being absolutely no stress, 10 being an overwhelming amount of stress. Once the current perceived stress number was determined, a therapist randomly picked from one of the four individual treatments; aromatherapy, guided meditation, color therapy, or nature pictures to use with the individual. The therapist followed the protocol for that treatment. A perceived second stress scale value was gathered for comparison following completion of the individual treatment.

The protocol for delivering aromatherapy was: Individuals were asked to close their eyes while seated and take several deep breaths in through their nose breathing in a blend of soothing essential oils. In an exemplary embodiment, the therapist put several drops of a selected soothing aromatherapy blend into their hands and held them in front of the participant and asked them to take two deep, slow breaths (in through the nose and out through the mouth). After the protocol, individual were asked to report their stress level.

The protocol for delivering color therapy was: Participants were sitting comfortably in a chair and shown one of two colors on an 8.5"×11" poster. For this experiment, only choices of orange or blue were provided. Participants were asked to focus on the color for 15 seconds and then report their stress level.

The protocol for delivering guided meditation was: Participants were asked to sit comfortably, close their eyes while a therapist read a guided meditation to the participant, which took about 30 seconds to deliver. The participants were asked to then report their stress level.

The protocol for delivering visual stimuli was: Participants were asked to view black and white pictures of a natural scene. They were asked to look at the picture for 15 seconds while sitting comfortably in a chair. Following the viewing, participants were asked to report the stress levels.

Treatments were provide by four trained therapists.

The therapist then provided an embodiment of method 100 in which the users selected a color from a color palate which consequently provided for the type of visual, scent, sound, and tactile stimulation to be provided to the user. Once method 100 was completed, the participant was again asked to provide their current stress level according to the 0-10 scale. The therapist recorded their response.

Results: A comparison is done between each of the individual treatments with method 100. Participants' pre-treatment stress levels were found to have an average stress level of 5.11 on a scale of 0 to 10. The combined average stress reduction level of the 4 individual treatments is 0.48. The average stress reduction level following the embodiment of method 100 is 3.3 from the pre-treatment stress level showing that method 100 is about 6.9 times more effective than the individual stress reduction methods at reducing perceived stress.

A breakdown of the results of the individual treatment of aromatherapy vs. method 100 is shown in table 1 below.

TABLE 1

| Cohen's PSS score | Pre-treatment stress level | Aromatherapy Post-treatment level | Individual treatment difference | Post Method 100 stress level | Difference after Method 100 |
|---|---|---|---|---|---|
| 26 | 6 | 6 | 0 | 2 | 4 |
| 21 | 5 | 5 | 0 | 2 | 3 |
| 14 | 4 | 4 | 0 | 1 | 3 |
| 27 | 7 | 5 | 2 | 3 | 4 |
| 18 | 4 | 4 | 0 | 2 | 2 |
| 28 | 8 | 7 | 1 | 2 | 6 |

Table 1 shows an average reduction of perceived stress from pre to post individual treatment of aromatherapy to be 0.48 while the average reduction from pre-treatment perceived stress level to after method 100 treatment was 3.67. Method 100 is shown to be 7 times more effective than aromatherapy alone.

A breakdown of the results of the individual treatment of color therapy vs. method 100 is shown in table 2 below.

TABLE 2

| Cohen's PSS score | Pre-treatment stress level | Color Therapy Post treatment stress level | Difference individual treatment | Post Method 100 level | Difference after Method 100 |
|---|---|---|---|---|---|
| 20 | 7 | 7 | 0 | 3 | 4 |
| 23 | 5 | 4 | 1 | 2 | 3 |
| 14 | 6 | 6 | 0 | 4 | 2 |
| 2 | 1 | 1 | 0 | 0 | 1 |
| 3 | 4 | 4 | 0 | 0 | 4 |
| 14 | 4 | 4 | 0 | 0 | 4 |

Table 2 shows an average reduction of 0.17 when color therapy is used alone. However, these participants reported an average stress reduction of 3 when using method 100. Method 100 is shown to be more than 17 times effective than color therapy alone.

A breakdown of the results of the individual treatment of guided visualization/mediation vs. method 100 is shown in table 3 below.

TABLE 3

| Cohen's PSS Score | Pre-treatment stress level | Post Guided Visualization treatment stress level | Difference individual treatment | Post Method 100 stress level | Difference after Method 100 |
|---|---|---|---|---|---|
| 19 | 6 | 4 | 2 | 2 | 4 |
| 29 | 9 | 8 | 1 | 6 | 3 |
| 8 | 2 | 1 | 1 | 0 | 2 |
| 23 | 5 | 4 | 1 | 1 | 4 |
| 9 | 4 | 3 | 1 | 1 | 3 |
| 21 | 7 | 7 | 0 | 3 | 4 |

Table 3 shows an average reduction in perceived stress level in participants who received guided meditation of 1.0. When the same participants used method 100 there was an average of 3.33. Method 100 is shown as more than 3 times effective in reducing stress than guided meditation alone.

A breakdown of the results of the individual treatment of visualization vs. method 100 is shown in table 4 below.

TABLE 4

| Cohen's PSS | Pre-treatment stress level | Post Visualization treatment stress level | Difference individual treatment | Post Method 100 stress level | Difference after Method 100 |
|---|---|---|---|---|---|
| 32 | 7 | 7 | 0 | 4 | 3 |
| 20 | 4 | 4 | 0 | 1 | 3 |
| 16 | 4 | 3 | 1 | 0 | 4 |
| 19 | 7 | 6 | 1 | 1 | 6 |
| 21 | 5 | 5 | 0 | 2 | 3 |
| 15 | 4 | 4 | 0 | 0 | 4 |
| 15 | 5 | 4 | 1 | 2 | 3 |
| 11 | 1 | 1 | 0 | 0 | 1 |
| 18 | 7 | 7 | 0 | 5 | 2 |

Table 4 shows that participants who were shown black and white nature photos reported an average reduction in stress of 0.33. The same participants reported an average stress reduction of 3.22 after using method 100. Method 100 is about 10 times more effective than nature pictures alone.

Overall, the results of experiment 1 demonstrate markedly reduced perceived stress levels when users use method 100 verses being given individual treatments.

Experiment 2: Reducing Stress in the Workplace:
Pre and Post Stress Levels in Hospital Staff Utilizing Method 100

The goals of experiment 2 were to a) determine the effectiveness of method 100 as a modality for stress reduction, b) measure the subjective stress levels of workers in a hospital setting pre and post treatment, c) determine the amount of time to significantly reduce stress level using the method 100 treatment protocol, and d) find a cost effective client-centered solution to the problem of stress in the workplace.

As discussed above, method 100 is a stress reduction method that uses a synergistic combination of aromatherapy, visualization, and color therapy. Each participant was asked their age, gender, occupation, and current stress level on a 0-10 scale, 0 being no stress, 10 being max stress.

Next, individuals were asked to choose one of seven images provided as part of method 100. Individuals then entered the tent where they sat in an office chair next to a treatment specialist. The treatment specialists performed a three minute session using method 100 on the individual based upon the image selected by each individual. After completion of the multi-sensory treatment, participants were asked to restate their stress level and were allowed to make comments about their experience. The characteristics of the participants are detailed below in Table 5.

TABLE 5

Total of 43 subjects

| | |
|---|---|
| Gender: | Men (3), Women (40) |
| Occupation: | Administrative (24), Clinical (19) |
| Age: | 20-29 years (4) |
| | 30-39 years (8) |
| | 40-49 years (8) |
| | 50-59 years (13) |
| | 60-69 years (9) |
| | 70+ years (1) |
| Stress Level Average Pre Treatment: | 6 |
| Stress Level Average Post Treatment: | 2 |

Results: The average stress level prior to treatment was 6/10. The average stress level post treatment was 2/10. This shows a significant reduction in the stress levels of workers after a three minute treatment using and exemplary embodiment of method 100. Notably, all participants reported a reduction in stress levels. Overall, there was a clinical reduction in perceived stress levels of about 67% on average.

Figure 3:
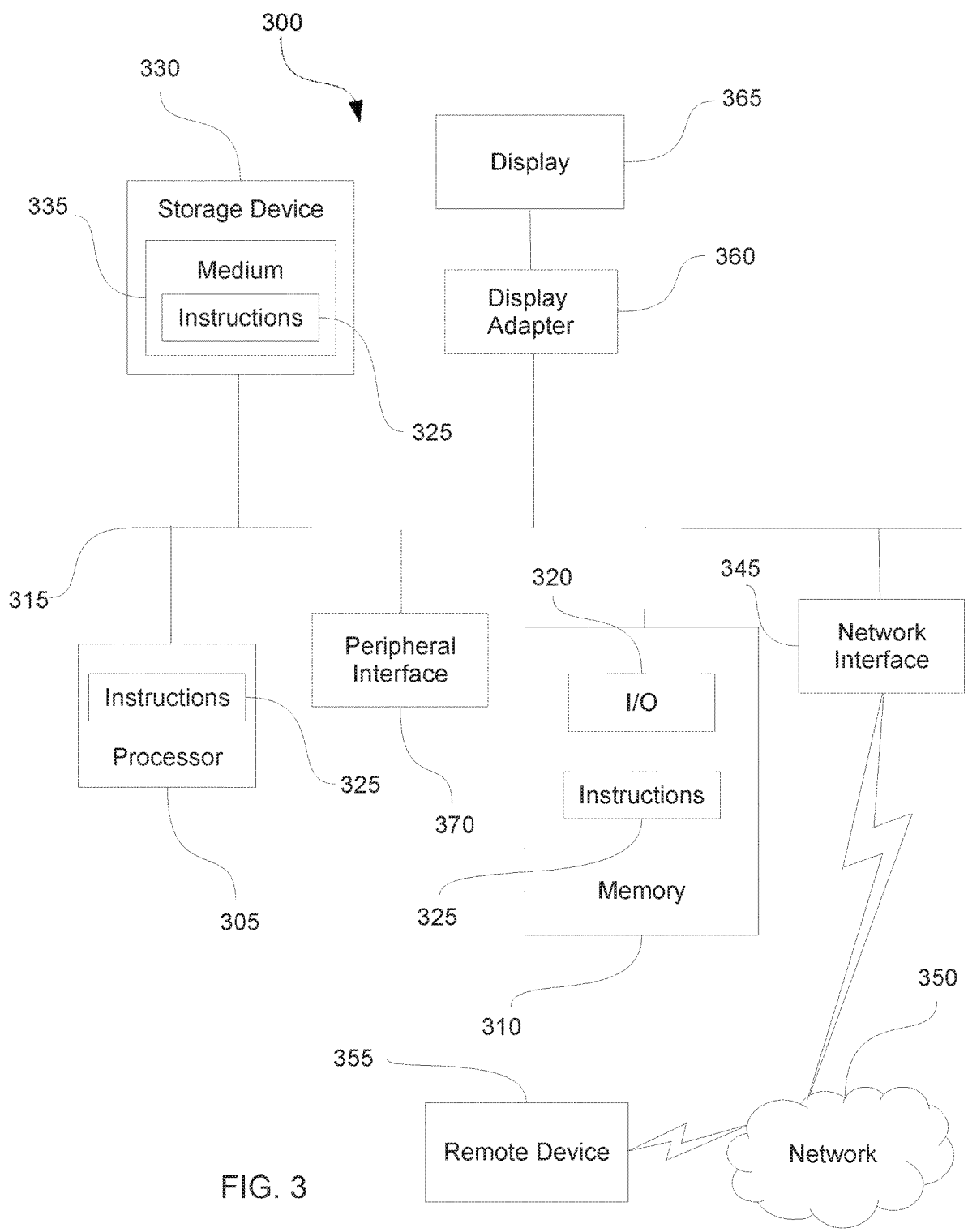
FIG. 3 shows a diagram of an exemplary system usable for implementing the method described herein.

FIG. 3 shows a diagrammatic representation of one embodiment of computing system in the exemplary form of a system 300, e.g., computing device 204 (FIG. 2), within which a set of instructions for causing a processor, such as processor 208 (FIG. 2), to perform any one or more of the aspects and/or methodologies, such as the method (method 100) or system (system 200) described herein. It is also contemplated that multiple computing devices, or mobile devices, or combinations of computing devices and mobile devices, may be utilized to implement a specially configured set of instructions for implementing the treatment method or any one or more of the aspects and/or methodologies of the present disclosure.

System 300 includes a processor 305 and a memory 310 that communicate with each other via a bus 315. Bus 315 may include any of several types of communication structures including, but not limited to, a memory bus, a memory controller, a peripheral bus, a local bus, and any combinations thereof, using any of a variety of architectures. Memory 310 may include various components (e.g., machine-readable media) including, but not limited to, a random access memory component (e.g., a static RAM "SRAM", a dynamic RAM "DRAM", etc.), a read-only component, and any combinations thereof. In one example, a basic input/output system 320 (BIOS), including basic routines that help to transfer information between elements within device 300, such as during start-up, may be stored in memory 310. Memory 310 may also include (e.g., stored on one or more machine-readable media) instructions (e.g., software) 325 embodying any one or more of the aspects and/or methodologies of the present disclosure. In another example, memory 310 may further include any number of program modules including, but not limited to, an operating system, one or more application programs, other program modules, program data, and any combinations thereof.

Device 300 may also include a storage device 330. Examples of a storage device (e.g., storage device 330) include, but are not limited to, a hard disk drive for reading from and/or writing to a hard disk, a magnetic disk drive for reading from and/or writing to a removable magnetic disk, an optical disk drive for reading from and/or writing to an optical media (e.g., a CD, a DVD, etc.), a solid-state memory device, and any combinations thereof. Storage device 330 may be connected to bus 315 by an appropriate interface (not shown). Example interfaces include, but are not limited to, SCSI, advanced technology attachment (ATA), serial ATA, universal serial bus (USB), IEEE 3395 (FIREWIRE), and any combinations thereof. In one example, storage device 330 may be removably interfaced with device 300 (e.g., via an external port connector (not shown)). Particularly, storage device 330 and an associated non-transitory machine-readable medium 335 may provide nonvolatile and/or volatile storage of machine-readable instructions, data structures, program modules, and/or other data for device 300. In one example, instructions 325 may reside, completely or partially, within non-transitory machine-readable medium 335. In another example, instructions 325 may reside, completely or partially, within processor 305.

Device 300 may also include a connection to one or more systems or software modules that carry out the methods discussed herein. Any system or device may be interfaced to bus 315 via any of a variety of interfaces (not shown), including, but not limited to, a serial interface, a parallel interface, a game port, a USB interface, a FIREWIRE interface, a direct connection to bus 315, and any combinations thereof. Alternatively, in one example, a user of device 300 may enter commands and/or other information into device 300 via an input device (not shown). Examples of an input device include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof.

A user may also input commands and/or other information to device 300 via storage device 330 (e.g., a removable disk drive, a flash drive, etc.) and/or a network interface device 345. A network interface device, such as network interface device 345, may be utilized for connecting device 300 to one or more of a variety of networks, such as network 350, and one or more remote devices 355 connected thereto. Examples of a network interface device include, but are not limited to, a network interface card, a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a direct connection between two computing devices, and any combinations thereof. A network, such as network 350, may employ a wired and/or a wireless mode of communication. In general, any network topology may be used. Information (e.g., data, instructions 325, etc.) may be communicated to and/or from device 300 via network interface device 355.

Device 300 may further include a video display adapter 360 for communicating a displayable image to a display device 365. Examples of a display device 365 include, but are not limited to, a liquid crystal display (LCD), a cathode ray tube (CRT), a plasma display, and any combinations thereof.

In addition to display device 365, device 300 may include a connection to one or more other peripheral output devices including, but not limited to, an audio speaker, a printer, and any combinations thereof. Peripheral output devices may be connected to bus 315 via a peripheral interface 370. Examples of a peripheral interface include, but are not limited to, a serial port, a USB connection, a FIREWIRE connection, a parallel connection, a wireless connection, and any combinations thereof.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A treatment method for treating stress in a person in need thereof comprising:
   receiving, as an input, information related to the stress experienced by the person;
   selecting a stress modifier program based upon the information; and
   exposing the person to synergistically effective amount of a multi-sensory stimuli, the multi-sensory stimuli being associated with the stress modifier program, wherein the multi-sensory stimuli include at least one visual stimulus, at least one olfactory stimulus, at least one auditory stimulus, and at least one tactile stimulus, wherein the exposing is completed in about three minutes and results in a stress reduction above 60% percent.

2. A treatment method according to claim 1, further including providing a recall stimulus, wherein the recall stimulus has a direct relationship to at least one of the at least one visual stimulus, the at least one olfactory stimulus, the at least one auditory stimulus, and the at least one tactile stimulus.

3. A treatment method according to claim 2, wherein the recall stimulus is a scented wristband.

4. A treatment method according to claim 1, wherein the information includes the type of stress experienced by the person.

5. A treatment method according to claim 1, wherein the information includes a color selection.

6. A treatment method according to claim 1, wherein the olfactory stimulus is an essential oil applied to the person.

7. A treatment method according to claim 1, wherein the auditory stimulus is a guided visualization.

8. A treatment method according to claim 1, wherein the auditory stimulus is a music.

9. A treatment method according to claim 1, wherein the auditory stimulus is both a guided visualization and a music.

10. A system for treatment of stress in a person, the system comprising:
    a multi-sensory stimuli delivery system; and
    a computing device in communication with the multi-sensory stimuli delivery system including a processor and a database, the database including a media data portion, a visual data portion, an olfactory data portion, and a tactile data portion, the processor including a set of instructions to:
    receive, as an input, information related to the stress experienced by the person; and
    determine a stress modifier program based upon the information, direct the multi-sensory stimuli delivery system to expose the person to multi-sensory stimuli, the multi-sensory stimuli being associated with the stress modifier program, wherein the multi-sensory stimuli include at least one visual stimulus, at least one olfactory stimulus, and at least one auditory stimulus, and wherein the exposing to the person is completed in about three minutes and results in a stress reduction above 60% percent.

11. A system according to claim 10, wherein the multi-sensory stimuli delivery system provides a tactile stimulus to the person in conjunction with the multi-sensory stimuli.

12. A system according to claim 10, wherein the multi-sensory stimuli delivery system includes a virtual reality headset.

13. A system according to claim 10, wherein the computing device further includes a profile library, the profile library including information related to use of the system by the person, and wherein the stress modifier program is based on the information and the profile library.

14. A system according to claim 10, wherein the information includes a color selection.

15. A system according to claim 10, wherein the olfactory stimulus is an essential oil applied to the person.

16. A system according to claim 10, wherein the auditory stimulus is a guided visualization.

17. A system according to claim 10, further including a recall stimulus, wherein the recall stimulus has a direct relationship to at least one of the at least one visual stimulus, the at least one olfactory stimulus, and the at least one auditory stimulus.

18. A system according to claim 10, wherein the recall stimulus is a scented wristband.

* * * * *